United States Patent [19]

Kolling et al.

[11] 4,021,571

[45] May 3, 1977

[54] SUBSTITUTED PHENYLISOTHIOUREAS AND PROCESSES FOR THEIR PREPARATION AND USE

[75] Inventors: Heinrich Kolling, Haan; Herbert Thomas, Wuppertal; Arno Widdig, Blecher; Hartmund Wollweber, Wuppertal, all of Germany

[73] Assignee: Bayer Aktiengesellschaft, Germany

[22] Filed: June 4, 1976

[21] Appl. No.: 693,097

Related U.S. Application Data

[62] Division of Ser. No. 595,040, July 11, 1975.

[30] Foreign Application Priority Data

July 16, 1974 Germany ............................ 2434183

[52] U.S. Cl. .......................... 424/300; 260/465 X; 260/465 F; 260/468 E; 260/470; 260/471 A; 260/558 R; 260/558 S; 260/559 R; 260/566 R; 424/303; 424/304; 424/309; 424/320; 424/322; 424/327; 424/335

[51] Int. Cl.[2] ............................................ A01N 9/12

[58] Field of Search ................... 260/470; 424/300

[56] References Cited

UNITED STATES PATENTS

| | | | |
|---|---|---|---|
| 3,649,679 | 3/1972 | Marshall | 260/470 X |
| 3,766,243 | 10/1973 | Widdig et al. | 260/470 |
| 3,843,215 | 10/1974 | Widdig et al. | 260/470 |

*Primary Examiner*—Howard T. Mars

[57] ABSTRACT

N-[2-(Substituted amido)phenyl]-N'-carbonyl-S-substituted isothioureas bearing an optionally substituted phenoxy, phenylthio, phenylsulfinyl or phenylsulfonyl group in the 4- or 5-position of the 2-(substituted amido)-phenyl group are anthelmintic agents. The compounds, of which N-(2-acetamido-4-phenoxyphenyl)-N'-carbomethoxy-S-methylthiourea is a typical example, are prepared through the reaction of S-substituted N-(mercaptohalomethylene)carbamic acid ester and an appropriately substituted 2-aminoanilide, or through alkylation of the corresponding S-unsubstituted thiourea.

20 Claims, No Drawings

SUBSTITUTED PHENYLISOTHIOUREAS AND PROCESSES FOR THEIR PREPARATION AND USE

This is a division of Ser. No. 595,040 filed July 11, 1975.

DETAILED DESCRIPTION

The present invention pertains to substituted phenylisothioureas, to methods for their preparation and use as anthelmintics, and to compositions thereof useful in such use.

The present invention pertains to anthelmintic phenyl-isothioureas of the formula:

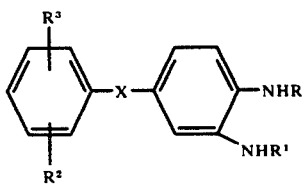

wherein X is oxygen, sulfur, sulfinyl or sulfonyl;
one of R and $R^1$ is $-COR^4$ and the other is

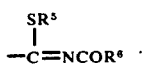

in which
$R^4$ is hydrogen or an unsubstituted or substituted alkyl, cycloalkyl, alkoxy, aryl, aralkyl or amino group;
$R^5$ is an unsubstituted or substituted alkyl, alkenyl, alkynyl or aryl group; and
$R^6$ is hydrogen or an unsubstituted or substituted alkyl, cycloalkyl, alkenyl, alkynyl, aryl, alkoxy, alkenyloxy or alkynyloxy group; and
each of $R^2$ and $R^3$ independent of the other is hydrogen, halogeno, cyano, or an unsubstituted or substituted alkyl, alkoxy, alkylthio, halogenoalkyl, amino or carbalkoxy group.

The foregoing isothioureas can be depicted in two tautomeric forms, as shown below for the isothiourea moiety only:

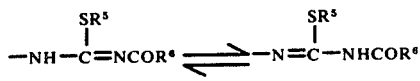

While for consistency and conciseness the structural formulas have been shown in only one of the foregoing ways, it will be appreciated that the actual compounds are inclusive of all tautomeric forms.

In the present context, the optionally-substituted alkyl groups embraced by $R^2$, $R^3$, $R^4$, $R^5$ and $R^6$ are straight- or branched hydrocarbon chains containing from 1 to 6, especially from 1 to 4, carbon atoms, as for example methyl, ethyl, n- and i-propyl, and n-, i- and t-butyl groups.

Alkenyl groups embraced by $R^5$ and $R^6$ will be straight- or branched chained and contain from 2 to 6, especially 2 to 4, carbon atoms. Ethenyl, propenyl-(1), propenyl-(2) and butenyl-(3) can be mentioned as examples.

Alkynyl groups embraced by $R^5$ and $R^6$ will be straight- or branched chained and contain from 2 to 6, will be straight- or branched chained and contain from 2 to 6, especially from 2 to 4, carbon atoms. Ethynyl, propynyl-(1), propynyl-(2) and butyinyl-(3) are typical.

Alkoxy groups embraced by $R^2$, $R^3$, $R^4$ and $R^6$ are straight- or branched chained with from 1 to 6, especially from 1 to 4, carbon atoms. Methoxy, ethoxy, n- and i-propoxy and n-, i- and t-butoxy may be mentioned as examples.

Alkylthio groups embraced by $R^2$ and $R^3$ are straight- or branched chained with from 1 to 6, especially from 1 to 4, carbon atoms. Methylthio, ethylthio, n- and i-propylthio and n-, i- and t-butylthio may be mentioned as examples.

Acyl groups embraced by $R^2$ and $R^3$ contain from 1 to 6, especially 2 to 4, carbon atoms. Formyl, acetyl, propionyl, n-butyryl and i-butyryl can be mentioned as examples.

Carbalkoxy groups embraced by $R^2$ and $R^3$ can be straight or branched chained with from 2 to 7, especially 2 to 5, carbon atoms. Carbomethoxy, carbethoxy, carbo-n- and i-propoxy and carbo-n-, -i- and -t-butoxy can be mentioned as examples.

The halogenoalkyl groups embraced by $R^2$ and $R^3$ contain from 1 to 4, especially 1 or 2, carbon atoms and preferably from 1 to 5, especially 1 to 3, identical or different halogen atoms, the halogen atoms being fluorine, chlorine and bromine, especially fluorine and chlorine. Perhalogenated alkyl groups are preferred. Trifluoromethyl, chlorodifluoromethyl, bromomethyl, 2,2,2-trifluoroethyl and pentafluoroethyl can be mentioned as examples.

Halogeno embraced by $R^2$ and $R^3$ is fluoro, chloro, bromo or iodo, especially fluoro, chloro and bromo.

Aryl groups embraced by $R^4$ and $R^6$ contain from 6 to 10 carbon atoms in the aromatic ring system. Optionally-substituted phenyl and naphthyl can be mentioned as examples.

Aralkyl groups embraced by $R^4$ and $R^6$ are optionally-substituted in the aryl part or alkyl part with 6 to 10, preferably 6, carbon atom in the aryl part and from 1 to 4 especially 1 or 2, carbon atoms in the alkyl part. The alkyl part can be straight- or branched chained. Optionally-substituted benzyl and phenylethyl are typical.

Cycloalkyl groups embraced by $R^4$ and $R^6$ are monocyclic, bicyclic or tricyclic cycloalkyl groups with from 3 to 10, especially 3 to 6, carbon atoms. Cyclopropyl, cyclobutyl, cyclopentyl, cyclohexyl, cycloheptyl, bicyclo [2.2.1]-heptyl, bicyclo[2.2.2]octyl and adamantyl are examples.

Alkenyloxy groups embraced by $R^6$ are straight- or branched chained from 2 to 6, especially 2 to 4, carbon atoms. Ethenyloxy, propenyl-(1)-oxy, propenyl-(2)-oxy and butenyl-(3)-oxy are examples.

Alkynyloxy groups embraced by $R^6$ are straight- or branched chained with from 2 to 6, especially 2 to 4, carbon atoms. Ethynyloxy, propynyl-(1)-oxy, propynyl-(2)-oxy and butynyl-(3)-oxy are examples.

The foregoing groups embraced by $R^2$, $R^3$, $R^4$, $R^5$ and $R^6$, other than hydrogen and halogeno, can in turn be optionally substituted as for example by acyl with 2 to 4 carbon atoms, carbalkoxy groups with 2 to 4 carbon atoms, alkoxyalkyl groups with 1 to 4 carbon atoms in the alkoxy part and 1 to 4 carbon atoms in the alkyl part, and aralkyl groups with 1 to 4 carbon atoms in the alkyl part and 6 carbon atoms in the aryl part.

In one embodiment, the present invention pertains to compounds in which $R^4$ is alkyl of 1 to 6 carbon atoms, cycloalkyl of 3 to 10 carbon atoms, alkoxy of 1 to 6 carbon atoms, phenyl, phenylalkyl of 7 to 12 carbon atoms, alkoxyalkyl of 2 to 12 carbon atoms, phenoxyalkyl of 7 to 12 carbon atoms, amino alkylamino of 1 to 6 carbon atoms or dialkylamino wherein each alkyl group contains 1 to 6 carbon atoms;

$R^5$ is alkyl of 1 to 6 carbon atoms, alkenyl of 2 to 6 carbon atoms or alkynyl of 2 to 6 carbon atoms; and $R^6$ is hydrogen, alkyl of 1 to 6 carbon atoms, cycloalkyl of 3 to 10 carbon atoms, alkenyl of 2 to 6 carbon atoms, alkynyl of 2 to 6 carbon atoms, alkoxy of 1 to 6 carbon atoms, alkenyloxy of 2 to 6 carbon atoms, alkynyloxy of 2 to 6 carbon atoms, phenyl, phenylalkyl of 7 to 12 carbon atoms, phenoxyalkyl of 7 to 12 carbon atoms, alkoxyalkyl of 2 to 12 carbon atoms or alkoxyalkoxy of 2 to 12 carbon atoms;

each of $R^2$ and $R^3$ independent of the other is hydrogen, halogeno, cyano, alkyl of 1 to 6 carbon atoms, alkoxy of 1 to 6 carbon atoms, alkylthio of 1 to 6 carbon atoms, trifluoromethyl, alkanoyl of 1 to 6 carbon atoms, amino, alkanoylamino of 1 to 6 carbon atoms, or carbalkoxy of 2 to 7 carbon atoms.

In a further embodiment, the present invention pertains to compounds in which $R^4$ is alkyl of 1 to 6 carbon atoms, cycloalkyl of 3 to 7 carbon atoms, alkoxy of 1 to 4 carbon atoms, alkenyl of 2 to 4 carbon atoms, alkynyl of 2 to 4 carbon atoms, alkoxyalkyl of 2 to 8 carbon atoms, phenyl, benzyl or phenethyl;

$R^5$ is alkyl of 1 to 4 carbon atoms, alkenyl of 2 to 4 carbon atoms, or alkynyl of 2 to 4 carbon atoms;

$R^6$ is hydrogen, alkyl of 1 to 4 carbon atoms, cycloalkyl of 3 to 7 carbon atoms, alkoxy of 1 to 4 carbon atoms, alkenyl of 2 to 4 carbon atoms, alkynyl of 2 to 4 carbon atoms, alkenyloxy of 2 to 4 carbon atoms, alkynyloxy of 2 to 4 carbon atoms, alkoxyalkyl of 2 to 8 carbon atoms, alkoxyalkoxy of 2 to 8 carbon atoms, phenyl, benzyl or phenethyl; and each of $R^2$ and $R^3$ independent of the other is hydrogen, fluoro, chloro, bromo, cyano, alkyl of 1 to 4 carbon atoms, alkoxy of 1 to 4 carbon atoms, alkylthio of 1 to 4 carbon atoms, trifluoromethyl, alkanoyl of 2 to 4 carbon atoms, amino, alkanoylamino of 2 to 4 carbon atoms or carbalkoxy of 2 to 7 carbon atoms.

In a further embodiment, the present invention pertains to compounds in which $R^4$ is alkyl of 1 to 6 carbon atoms, alkoxyalkyl of 2 to 8 carbon atoms, cycloalkyl of 3 to 7 carbon atoms, phenyl, phenoxyalkyl of 7 to 12 carbon atoms or alkylamino of 1 to 6 carbon atoms; or alkylamino of 1 to 6 carbon atoms;

$R^5$ is alkyl of 1 to 4 carbon atoms; and $R^6$ is alkoxy of 1 to 4 carbon atoms.

In a further embodiment, the present invention pertains to compounds in which X is oxygen.

In a further embodiment, the present invention pertains to compounds in which X is sulfur.

In a further embodiment, the present invention pertains to compounds in which X is sulfinyl.

In a further embodiment, the present invention pertains to compounds in which X is sulfonyl.

X can be linked to either the 4- or the 5-position of the phenylisothiourea.

The phenylisothioureas according to the present invention are anthelmintic agents, showing significantly greater activity in this regard than such commercially available agents such as 2-thiazol-4-ylbenzimidazole (thiabendazole).

The compounds are prepared by a. reacting a thiourea of the formula:

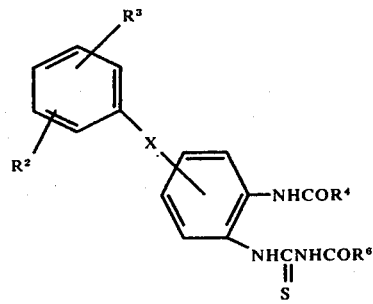

in which $R^2$, $R^3$, $R^4$, $R^6$ and X are as herein defined, with an alkylating agent of the formula:

$R^5-Y$ in which Y is a reactive halogen, alkylsulfate or arylsulfonate, in the presence of a diluent and a base, or b. reacting an aniline compound of the formula:

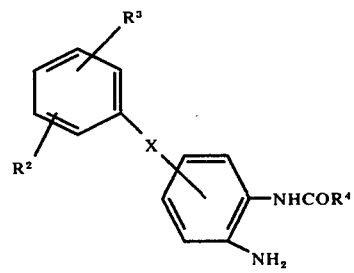

in which $R^2$, $R^3$, $R^4$ and $R^5$ are as herein defined, with a carbamic acid ester of the formula:

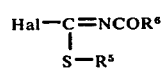

in which $R^5$ and $R^6$ are as herein defined and Hal is halogen, in the presence of a base and a diluent.

Typical alkylating agents include methyl iodide, ethyl iodide, isopropyl iodide, cyclohexyl bromide, dimethyl sulfate, toluene sulfonic acid methyl ester, allyl bromide, benzyl chloride and the like.

Suitable bases for the foregoing reactions include inorganic hydroxides, carbonates and bicarbonates such as sodium hydroxide, potassium hydroxides, sodium carbonate, sodium bicarbonate and the like, as well as organic amines such as triethylamine, pyridine, collidine and the like. Substantially equimolar amounts of the two reactants are employed with the reaction being conducted at temperatures of from −10° C to about +40° C, preferably from about 0° to 30° C. A diluent or solvent is employed such as an alcohol, as for example methanol, ethanol or isopropanol, a ketone as for example acetone, methylethyl ketone, a sulfoxide such as dimethylsulfoxide, an amide such as dimethylformamide or a nitrile such as acetonitrile. The medium can be aqueous utilizing water or one of the foregoing water-miscible solvents in combination with water. the product can be isolated and purified in the conventional manner, e.g. concentration by evaporation of the solvent, precipitation by addition to water, filtration and recrystallization.

The first reaction may be typified as follows, utilizing N-(2-acetamido-4-phenoxyphenyl)-N'-carbomethoxythiourea, methyl iodide and sodium hydroxide as representative reactants:

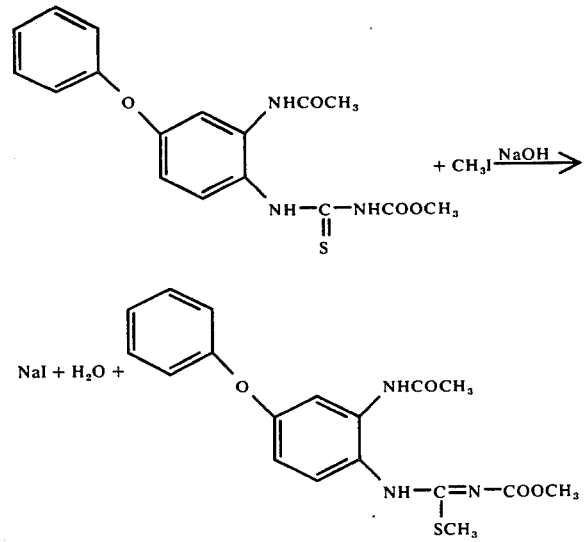

The second reaction may be typified as follows, utilizing 2-propionamido-4-phenylthioaniline, N-(methylmercaptochloromethylene)carbamic acid methyl ester and triethylamine as representative reactants:

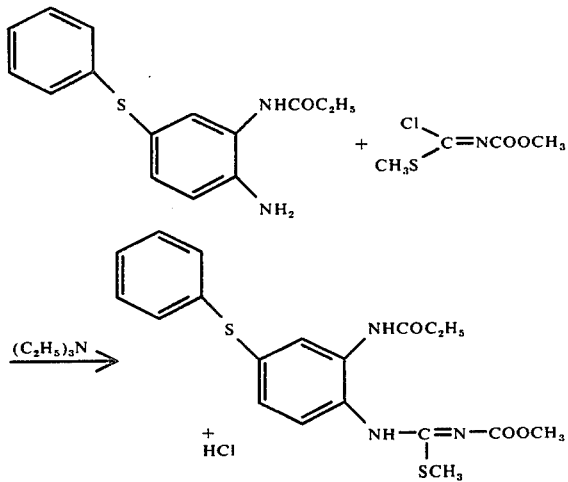

Typical thioureas which can be employed in the first of these processes include: N-(2-acetamido-4-phenoxyphenyl)-N'-methoxycarbonylthiourea, N-(2-acetamido-4-phenoxy-phenyl)-N'-ethoxycarbonylthiourea, N-(2-acetamido-4-phenoxy-phenyl)-N'-isopropoxycarbonylthiourea, N-(2-acetamido-4-phenoxy-phenyl)-N'-sec-butoxycarbonylthiourea, N-(2-propionamido-4-phenoxyphenyl)-N'-methoxycarbonylthiourea, N-(2-butyramido-4-phenoxyphenyl)-N'-methoxycarbonylthiourea, N-(2-isobutyramido-4-phenoxyphenyl)-N'-methoxycarbonylthiourea, N-(2-valeramido-4-phenoxyphenyl)-N'-methoxycarbonylthiourea, N-(isovaleramido-4-phenoxyphenyl)-N'-methoxycarbonylthiourea, N-(2-caproamido-4-phenoxyphenyl)-N'-methoxycarbonylthiourea, N-(2-isocapro-amido-4-phenoxyphenyl)-N'-methoxycarbonylthiourea, N-(2-cyclo-pentanecarboxylic acid amido-4-phenoxyphenyl)-N'-methoxy-carbonylthiourea, N-(2-cyclohexanecarboxylic acid amido-4-phenoxyphenyl)-N'-methoxycarbonylthiourea, N-(2-phenyl-acetamido-4-phenoxyphenyl)-N'-methoxycarbonylthiourea, N-(2-phenoxyacetamido-4-phenoxyphenyl)-methoxycarbonylthiourea. N-(2-acetamido-4-phenylthiophenyl)-N'-methoxycarbonylthiourea, N-(2-acetamido-4-phenylthiophenyl)-N'-ethoxycarbonylthiourea, N-(2-acetamido-4-phenylthiophenyl)-N'-isopropoxycarbonylthiourea, N-(2-acetamido-4-phenylthiophenyl)-N'-sec-butoxycarbonylthiourea, N-(2-propionamido-4-phenylthiophenyl)-N'-methoxycarbonylthiourea, N-(2-butyramido-4-phenylthiophenyl)-N'-methoxycarbonylthiourea, N-(2-isobutyramido-4-phenylthiophenyl)-N'-methoxycarbonylthiourea, N-(2-valeramido-4-phenylthiophenyl)-N'-methoxycarbonylthiourea, N-(isovaleramido-4-phenylthiophenyl)-N'-methoxycarbonylthiourea, N-(2-caproamido-4-phenylthiophenyl)-N'-methoxycarbonylthiourea, N-(2-isocaproamido-4-phenylthiophenyl)-N'-methoxycarbonylthiourea, N-(2-cyclopentanecarboxylic acid amido-4-phenylthiophenyl)-N'-methoxycarbonylthiourea, N-(2-cyclohexanecarboxylic acid-amido-4-phenylthiophenyl)-N'-methoxycarbonylthiourea, N-(2-phenylacetamido-4-phenylthiophenyl)-N'-methoxycarbonylthiourea, N-(2-phenoxyacetamido-4-phenylthiophenyl)-N'-methoxycarbonylthiourea, N-(2-benzamido-4-phenylthiophenyl)-N'-methoxycarbonylthiourea, and N-(2-(2'-methylureido)-4-phenylthiophenyl)-N'-methoxycarbonylthiourea.

Typical aniline derivatives which can be employed in the second of these processes include: 2-amino-5-phenoxyacetanilide, 2-amino-5-phenoxypropionanilide, 2-amino-5-phenoxy-butyranilide, 2-amino-5-phenoxy-isobutyranilide, 2-amino-5-phenoxy-valeranilide, 2-amino-5-phenoxy-isovaleranilide, 2-amino-5-phenoxy-caproanilide, 2-amino-5-phenoxy-isocaproanilide, 2-amino-5-phenoxy-cyclopentanecarboxylic acid anilide, 2-amino-5-phenoxy-cyclohexanecarboxylic acid anilide, 2-amino-5-(4-chloro-phenoxy)-acetanilide, 2-amino-5-(3-chloro-phenoxy)-propionanilide, 2-amino-5-(3-chloro-phenoxy)-butyranilide, 2-amino-5-(3-chloro-phenoxy)-acetanilide, 2-amino-5-(2-chloro-phenoxy)-propionanilide, 2-amino-5-(2-chloro-phenoxy)-butyranilide, 2-amino-5-(2-chloro-phenoxy)-acetanilide, 2-amino-4-phenoxy-acetanilide, 2-amino-4-phenoxy-propionanilide, 2-amino-4-phenoxy-butyranilide, 2-amino-4-phenoxy-iso-butyranilide, 2-amino-4-phenoxy-valeranilide, 2-amino-4-phenoxy-isovaleranilide, 2-amino-4-phenoxy-caproanilide, 2-amino-4-phenoxy-iso-caproanilide, 2-amino-4-phenoxy-cyclopentanecarboxylic acid anilide, 2-amino-4-phenoxy-cyclohexanecarboxylic acid anilide, 2-amino-4-phenoxy-phenylacetanilide, 2-amino-4-phenoxy-phenoxyacetanilide, 2-amino-4-(4-chloro-phenoxy)-propionanilide, 2-amino-4-(4-chloro-phenoxy)-butyranilide, 2-amino-4-(4-chloro-phenoxy)-acetanilide, 2-amino-4-(3-chlorophenoxy)-propionanilide, 2-amino-4-(3-chloro-phenoxy)-butyranilide, 2-amino-4-(3-chloro-phenoxy)-acetanilide, 2-amino-4-(2-chloro-phenoxy)-propionanilide, 2-amino-4-(2-chloro-phenoxy)-butyranilide, 2-amino-4-(2-chloro-phenoxy)-acetanilide, 2-amino-4-(4-methoxyphenoxy)-propionanilide, 2-amino-4-(4-methoxy-phenoxy)-butyranilide, 2-amino-4-(4-methoxy-phenoxy)-acetanilide, 2-amino-4-(3-methoxy-phenoxy)-propionanilide, 2-amino-4-(3-methoxy-phenoxy)-butyranilide, 2-amino-4-(3-methoxy-phenoxy)-acetanilide. 2-amino-5-phenylthio-acetanilide, 2-amino-5-phenylthio-propionanilide, 2-amino-5-phenylthio-butyranilide, 2-amino-5-phenylthio-isobutyranilide, 2-amino-5-phenylthio-valeranilide, 2-amino-5-phenylthio-iso-valeranilide, 2-amino-5-phenylthio-caproanilide, 2-amino-5-phenylthio-iso-caproanilide, 2-amino-5-phenylthio-cyclopentanecarboxylic acid anilide, 2-amino-5-phenylthio-cyclohexanecarboxylic acid anilide, 2-amino-5-phenylthio-phenylacetanilide, 2-amino-5-phenylthio-phenoxyacetanilide, 2-amino-5-(4-chloro-phenylthio)-propionanilide, 2-amino-5-(4-chloro-phenylthio)-butyranilide, 2-amino-5-(4-chloro-phenyl-thio)-acetanilide, 2-amino-5-(3-chlorophenylthio)-propionanilide, 2-amino-5-(3-chloro-phenylthio)-butyranilide, 2-amino-5-(3-chloro-phenylthio)-acetanilide, 2-amino-5-(2-chloro-phenylthio)-propionanilide, 2-amino-5-(2-chloro-phenylthio)-butyranilide, 2-amino-5-(2-chloro-phenylthio)-acetanilide, 2-amino-5-(4-methoxy-phenylthio)-propionanilide, 2-amino-5-(4-methoxy-phenylthio)-butyranilide, 2-amino-5-(4-methoxy-phenylthio)-acetanilide, 2-amino-5-(3-methoxy-phenylthio)-propionanilide, 2-amino-5-(3-methoxy-phenylthio)-butyranilide, 2-amino-5-(3-methoxy-phenylthio)-acetanilide, 2-amino-5-(4-methylthio-phenylthio)-propionanilide, 2-amino-5-(4-methylthio-phenylthio)-butyranilide, 2-amino-5-(4-methylthio-phenylthio)-acetanilide, 2-amino-5-(3-methylthio-phenylthio)-propionanilide, 2-amino-5-(3-methylthio-phenylthio)-butyranilide, 2-amino-5-(3-methylthio-phenylthio)-acetanilide, 2-amino-4-phenylthio-acetanilide, 2-amino-4-phenylthio-propionanilide, 2-amino-4-phenylthiobutyranilide, 2-amino-4-phenylthio-iso-butranilide, 2-amino-4-phenylthio-valeranilide, 2-amino-4-phenylthio-iso-valeranilide, 2-amino-4-phenylthio-caproanilide, 2-amino-4-phenylthio-iso-caproanilide, 2-amino-4-phenylthio-cyclopentanecarboxylic acid anilide, 2-amino-4-phenylthio-cyclohexanecarboxylic acid anilide, 2-amino-4-phenylthio-phenylacetanilide, 2-amino-4-phenylthio-phenoxyacetanilide, 2-amino-4-(4-chloro-phenylthio)-propionanilide, 2-amino-4-(4-chlorophenylthio)-butyranilide, 1-amino-4-(4-chlorophenylthio)-acetanilide, 2-amino-4-(3-chloro-phenylthio)-propionanilide, 2-amino-4-(3-chloro-phenylthio)-butyranilide, 2-amino-4-(3-chloro-phenylthio)-acetanilide.

The thioureas and aniline derivatives utilized as starting materials are known or can be readily prepared by methods known to the art. For example, a 4-substituted nitroaniline can be acylated and the resultant 4-substituted nitroanilide then reduced as with Raney nickel or palladium/carbon to yield the desired aniline derivative. This in turn can be converted into the corresponding thiourea through treatment with an alkali metal thiocyanate and a halide of the formula $R^6COHal$ in which Hal is halogen. These reactions can be represented as follows:

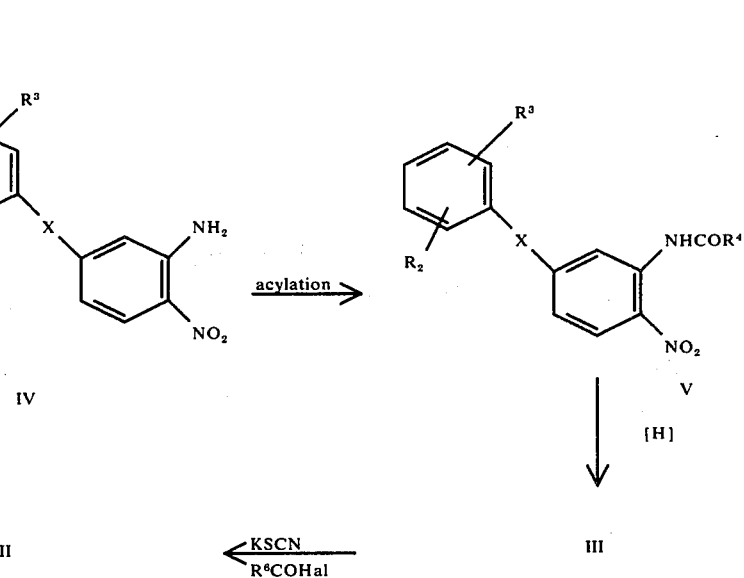

Those compounds wherein X is sulfinyl or sulfonyl can be obtained by oxidation of the corresponding compounds wherein X is sulfur. Oxidation with, for example, hydrogen peroxide in acetic acid or perbenzoic acid in dioxane or chloroform produces the corresponding sulfinyl compound whereas oxidation with hydrogen peroxide in glacial acetic acid at about 100° C yields the corresponding sulfonyl compound. The oxidation can be performed either on the nitroanilide intermediate or on the thiourea:

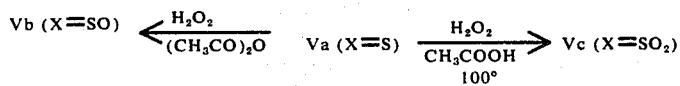

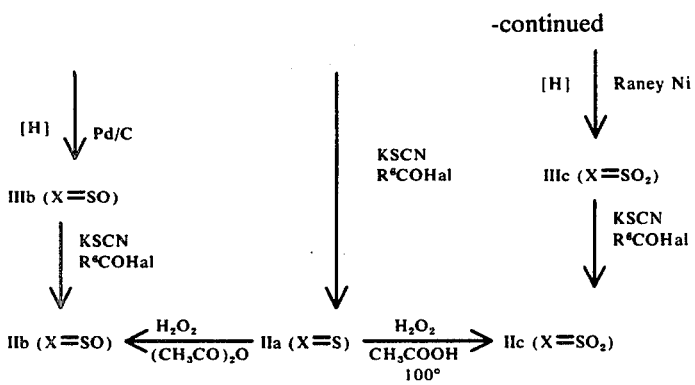

The compounds prepared in accordance with the invention show a surprisingly improved action against one or more of the following nematodes and cestodes:

1. Hookworms (for example *Uncinaria stenocephala*, *Ancylostoma caninum* and *Bunostomum trigonocephalum*).
2. Trichostrongylidae (for example *Nippostrongylus muris*, *Haemonchus contortus*, *Trichostrongylus colubriformis* and *Ostertagia circumcincta*).
3. Strongylidae (for example *Oesophagostomum columbianum*).
4. Rhabditidae (for example *Strongyloides ratti*).
5. Ascaridae (for example *Ascaris suum*, *Toxocara canis* and *Toxascaris leonina*).
6. Threadworms (for example *Aspiculuris tetraptera*).
7. Heterakidae (for example *Heterakis spumosa*).
8. Whipworms (for example *Trichuris muris*).
9. Filariae (for example *Litomosoides carinii* and *Dipetalonema witei*).
10. Cestodes (for example *Hymenolepis nana*, *Taenia pisiformis* and *Echinococcus multilocularis*).

The action of the compounds of the invention can be conveniently observed in vivo by oral and patenteral administration to test animals heavily infested with parasites.

In the biological test examples A to H inclusive, which follow, the action is recorded as follows: "Effective minimum dose (Red. > 90%) in mg/kg". This means that the minimum dosage in mg of active compound per kg of body weight of the test animal, which reduces the worm infection of the test animal by more than 90% ("Red. > 90%") is recorded.

EXAMPLE A

Hookworm test/dog

Dogs experimentally infected with *Uncinaria stenocephala* were treated at the end of the pre-patency period of the parasites.

The amount of active compound was administered orally as pure active compound in gelatine capsules.

The degree of action is determined by counting the worms expelled after the treatment and, after dissection, the worms remaining in the test animal, and calculating the percentage of worms expelled.

In the table which follows, the active compounds, the species of parasite and the minimum dosage which reduces the worm infection of the test animals by more than 90% (Red. > 90%") are recorded in comparison to Thiabendazole.

The dosage is given in mg of active compound per kg of body weight. The expression "3 × 2.5" means that 2.5 mg/kg were administered three times.

Table A

| Active compound according to the invention | Minimum effective dose (Red. 90%) mg/kg |
|---|---|
| ⟨phenyl⟩-S-⟨phenyl⟩-NH-C(SCH₃)=N-CO-OCH₃, NH-CO-C₃H₇ | 3 × 2.5 |
| Known preparation for comparison Thiabendazole | Uncinaria partial action only |

EXAMPLE B

Stomach and intestine worm test/sheep

Sheep experimentally infected with *Haemonchus contortus* or *Trichostrongylus colubriformis* were treated at the end of the pre-patency period of the parasites.

The amount of active compound was administered orally as pure active compound in gelatine capsules.

The degree of action is determined by quantitatively counting the worm eggs excreted with the faeces, before and after treatment.

Complete cessation of the excretion of eggs after the treatment denotes that the worms have been expelled or damaged to the extent that they can no longer produce eggs (effective dose).

Table B

| Active compound according to the invention | Parasite | Minimum effective dose (Red.>90%) in mg/kg |
|---|---|---|
| ⟨phenyl⟩-S-⟨phenyl⟩-NH-C(SCH₃)=N-CO-OCH₃, NH-CO-C₃H₇ | Haemonchus cont. | 2.5 |
| | Trichostrong. col. | 2.5 |

Table B-continued

| Active compound according to the invention | Parasite | Minimum effective dose (Red.>90%) in mg/kg |
|---|---|---|
| Phenyl-S-phenyl with NH—C(SCH₃)=N—CO—OCH₃ and NH—CO—C₂H₅ substituents | Haemonchus cont. Trichostrong. col. | 2.5 1 |
| Phenyl-O-phenyl with NH—C(SCH₃)=N—CO—OCH₃ and NH—CO—CH₃ substituents | Haemonchus cont. Trichostrong. col. | 5 5 |
| Phenyl-O-phenyl with NH—C(SCH₃)=N—CO—OCH₃ and NH—CO—C₂H₅ substituents | Haemonchus cont. Trichostrong. col. | 5 5 |
| Phenyl-O-phenyl with NH—C(SCH₃)=N—CO—OCH₃ and NH—CO—C₃H₇ substituents | Haemonchus cont. Trichostrong. col. | 5 2.5 |
| Phenyl-O-phenyl with NH—CO—C₂H₅ and NH—C(SCH₃)=N—CO—OCH₃ substituents | Haemonchus cont. Trichostrong. col. | 2.5 2.5 |
| Phenyl-S-phenyl with NH—C(SCH₃)=N—CO—OCH₃ and NH—CO—CH₂—OCH₃ substituents | Haemonchus cont. Trichostrong. col. | 1 1 |
| Known preparation for comparison (quinoxaline-thiazole structure) | Haemonchus cont. Trichostrong. col. | 50 25 |

EXAMPLE C

Strongyloides ratti/rat

Rats experimentally infected with Strongyloides ratti were treated at the end of the pre-patency period of the parasites. The amount of active compound was administered orally as an aqueous suspension.

The degree of action of the preparation is determined by counting, after dissection, the worms which have remained in the test animal, in comparison to untreated control animals, and calculating the percentage action therefrom.

Table C

| Active compound according to the invention | Minimum effective dose (Red. >90%) in mg/kg |
|---|---|
| Phenyl-S-phenyl with NH—C(SCH₃)=N—CO—OCH₃ and NH—CO—C₂H₅ substituents | 10 |
| Known preparation for comparison (quinoxaline-thiazole structure) | 25 |

EXAMPLE D

Round-worm test/rat

Rats experimentally infected with Ascaris suum were treated 1 to 3 days after infection. The amount of active compound was administered orally as an aqueous suspension.

The degree of action of the preparation is determined by counting, after dissection, the worms which have remained in the test animal, in comparison to untreated control animals, and calculating the percentage action therefrom.

Table D

| Active compound according to the invention | Minimum effective dose (Red. >90%) in mg/kg |
|---|---|
| Ph-S-C6H3(NH-C(SCH3)=N-CO-OCH3)(NH-CO-C3H7) | 10 |
| Ph-S-C6H3(NH-C(SCH3)=N-CO-OCH3)(NH-CO-C2H5) | 50 |
| Ph-O-C6H3(NH-C(SCH3)=N-CO-OCH3)(NH-CO-CH3) | 250 |
| Ph-O-C6H3(NH-C(SCH3)=N-CO-OCH3)(NH-CO-C3H7) | 100 |
| Ph-O-C6H3(NH-CO-C2H5)(NH-C(SCH3)=N-CO-OCH3) | 25 |
| Known preparation for comparison (quinoxaline-thiazole) | 500 |

EXAMPLE E

Trichuris muris/mouse

Mice experimentally infected with *Trichuris muris* were treated at the end of the pre-patency period of the parasites.

The amount of active compound was administered orally as an aqueous suspension.

The degree of action of the preparation is determined by counting, after dissection, the worms which have remained in the test animal, in comparison to untreated control animals, and calculating the percentage action therefrom.

Table E

| Active compound according to the invention | Minimum effective dose (Red. >90%) in mg/kg |
|---|---|
| Ph-O-C6H3(NH-C(SCH3)=N-CO-OCH3)(NH-CO-CH3) | 5 |
| Ph-O-C6H3(NH-C(SCH3)=N-CO-OCH3)(NH-CO-C2H5) | 2.5 |
| Ph-O-C6H3(NH-C(SCH3)=N-CO-OCH3)(NH-CO-C3H7) | 10 |
| Ph-O-C6H3(NH-C(SCH3)=N-CO-OCH3)(NH-CO-Ph) | 5 |
| Ph-S-C6H3(NH-C(SCH3)=N-CO-OCH3)(NH-CO-C3H7) | 2,5 |
| Ph-S-C6H3(NH-C(SCH3)=N-CO-OCH3)(NH-CO-C2H5) | 5 |
| Ph-O-C6H3(NH-CO-C2H5)(NH-C(SCH3)=N-CO-OCH3) | 1 |
| Known preparation for comparison (quinoxaline-thiazole) | inactive |

The compounds of the invention are employed to combat helmintic infestations, both prophylactically and therapeutically, in humans and other animals through administration thereto of an anthelmintically effective amount of one or more compounds. Generally such an amount will range from about 1 mg/kg to about 100 mg/kg of body weight, depending upon the stage and severity of the infestation. This range is of course merely a guideline and the actual dose should be titrated to the recipient keeping in mind his age, general health and body weight, the response to treatment and the type of formulation. At times less than 0.1 mg/kg will suffice while at others more than 50 mg/kg can be indicated. The total daily dose thus will generally be from about 50 mg to about 10 g, although here again this is merely a guideline.

The compounds of the present invention are administered parenterally or orally in any of the usual pharmaceutical forms. These include solid and liquid oral unit dosage forms such as tablets, capsules, powders, suspensions, solutions, syrups and the like, including sustained release preparations, and fluid injectable forms such as sterile solutions and suspensions. The term unit dosage form as used in this specification and the claims refer to physically discrete units to be administered in single or multiple dosage to animals, each unit containing a predetermined quantity of active material in association with the required diluent, carrier or vehicle. The quantity of active material is that calculated to produce the desired therapeutic effect upon administration of one or more of such units.

Powders are prepared by comminuting the compound to a suitable fine size and mixing with a similarly comminuted diluent pharmaceutical carrier such as an edible carbohydrate material as for example, starch. Sweetening, flavoring, preservative, dispersing and coloring agents can also be present.

Capsules are made by preparing a powder mixture as described above and filling formed gelatin sheaths. A lubricant such as talc, magnesium stearate and calcium stearate can be added to the powder mixture as an adjuvant before the filling operation; a glidant such as colloidal silica may be added to improve flow properties; a disintegrating or solubilizing agent may be added to improve the availability of the medicament when the capsule is ingested.

Tablets are made by preparing a powder mixture, granulating or slugging, adding a lubricant and disintegrant and pressing into tablets. A powder mixture is prepared by mixing the compound, suitably comminuted, with a diluent or base such as starch, sucrose, kaolin, dicalcium phosphate and the like. The powder mixture can be granulated by wetting with a binder such as syrup, starch paste, acacia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The medicaments can also be combined with free flowing inert carriers and compressed into tablets directly without going through the granulating or slugging steps. A protective coating consisting of a sealing coat of shellac, a coating of sugar or polymeric material and a polish coating of wax can be provided. Dyestuffs can be added to these coatings to distinguish different unit dosages.

Oral fluids such as syrups and elixirs can be prepared in unit dosage form so that a given quantity, e.g., a teaspoonful, contains a predetermined amount of the compound. Syrups can be prepared by dissolving the compound in a suitably flavored aqueous sucrose solution while elixirs are prepared through the use of a non-toxic alcoholic vehicle. Suspensions can be formulated by dispersing the compound in a non-toxic vehicle in which it is insoluble.

Fluid unit dosage forms for parenteral administration can be prepared by suspending or dissolving a measured amount of the compound in a non-toxic liquid vehicle suitable for injection such as an aqueous or oleaginous medium and sterilizing the suspension or solution. Alternatively a measured amount of the compound is placed in a vial and the vial and its contents are sterilized and sealed. An accompanying vial or vehicle can be provided for mixing prior to administration.

The following examples will serve to further illustrate the compound of the invention and the methods of preparation without being a limitation on the scope thereof, the scope being defined solely by the appended claims.

EXAMPLE 1

A. 2-Nitro-5-phenoxyacetanilide

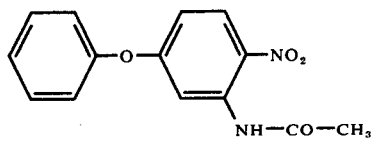

7.9 (0.1 mol) of acetyl chloride in 50 ml of dry benzene were added dropwise to a solution of 23 g (0.1 mol) of 2-nitro-5-phenoxy-aniline of melting point 142° C and 7.9 g (0.1 mol) of pyridine in 250 ml of dry benzene while stirring at room temperature. When the slightly exothermic reaction had subsided, the mixture was stirred for 1.5 hours at room temperature and a further 2 hours at the boil. Thereafter, the water-soluble pyridine hydrochloride which had separated out was filtered off hot, the solvent was distilled off in vacuo and the residue was thoroughly stirred with dilute hydrochloric acid, filtered off, dried and recrystallized from ethanol. 2-Nitro-5-phenoxy-acetanilide of melting point 90° C was obtained in a yield of 73% of theory.

B. 2-Amino-5-phenoxyacetanilide

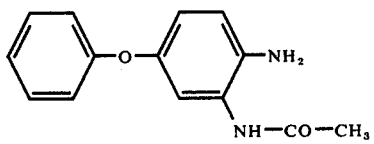

54.5 g (0.2 mol) of 2-nitro-5-phenoxy-acetanilide of melting point 90° C in 500 ml of tetrahydrofurane were hydrogenated with 5 g of Raney nickel at 50 atmospheres gauge pressure of hydrogen, for a reaction time of 1.5 hours. In the course thereof the temperature rose from 13° to 21° C; the $H_2$ consumption corresponded to the calculated amount. After cooling, the catalyst was filtered off, the solvent was evaporated and the residue was recrystallized from toluene. This gave 2-amino-5-phenoxy-acetanilide of melting point 120° in a yield of 77% of theory.

C. N-(2-Acetamido-4-phenoxyphenyl)-N'-carbomethoxy-S-methylisothiourea

A solution of 16.7 g (0.1 mol) of N-(methylmercaptochloromethylene)-carbamic acid methyl ester in a little chloroform is added dropwise to 24.2 g (0.1 mol) of 2-amino-5-phenoxyacetanilide and 10.1 g (0.1 mol) of triethylamine in 300 ml of dry chloroform while stirring at 0° C. After the dropwise addition, the temperature is allowed to rise to 20° C over the course of 2 hours and the mixture is then stirred for a further 3 hours at 25°–30° C. The chloroform is then stripped off in vacuo and the residue is stirred with water, filtered off and rinsed with ethanol and ether. Melting point: 186° C. Yield: 24 g (=64% of theory).

EXAMPLE 2

A. N-(2-Acetamido-4-phenoxyphenyl)-N'-carbomethoxy thiourea

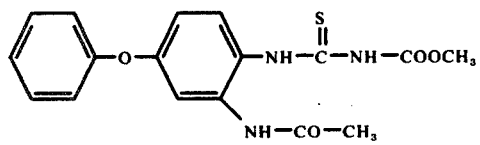

A solution which was prepared as follows was added dropwise to a solution of 121 g (0.5 mol) of 2-amino-5-phenoxyacetanilide of melting point 120° C in 1,000 ml of acetone, while stirring at room temperature:

94.5 g (1 mol) of chloroformic acid methyl ester were added to 97.2 g (1 mol) of potassium thiocyanate in 365 ml of dry acetone, while stirring and cooling with water. Towards the end of the dropwise addition, the temperature was allowed to rise to 40° C and the mixture was stirred for a further hour at this temperature and was then filtered (50% conversion is assumed).

After completion of the introduction of this solution of potassium thiocyanate and chloroformic acid methyl ester, the whole was stirred for 1 hour at room temperature and 4 hours at 60° C. It was then cooled to 10° C and the N-(2-acetamido-4-phenoxy-phenyl)-N'-methoxycarbonyl-thiourea which crystallized out was rinsed with a little acetone and dried. It was purified further by recrystallization from dioxane. Melting point 204° C (with decomposition), yield: 64 g.

B. N-(2-Acetamido-4-phenoxyphenyl)-N'-carbomethoxy-S-methylisothiourea

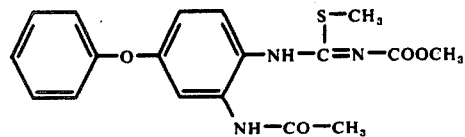

35.9 (0.1 mol) of N-(2-acetamido-4-phenoxyphenyl)-N'-methoxycarbonyl-thiourea and 5.4 g (0.1 mol) of sodium methylate in 300 ml of dimethylformamide are stirred at room temperature, 14.2 g (0.1 mol) of methyl iodide are then added dropwise and the mixture is stirred overnight at the same temperature.

After distilling off the solvent in vacuo, the residue consisting of the reaction product N-(2-acetamido-4-phenoxyphenyl)-N'-methoxycarbonyl-S-methylisothiourea is repeatedly extracted with water, filtered off and rinsed thoroughly with ethanol and ether. Melting point: 186° C.

EXAMPLE 3

By substituting 2-amino-5-phenoxypropionanilide, m.p. 122° C, for 2-amino-5-phenoxyacetanilide in the procedure of Example 1, part C, there is obtained N-(2-propionamido-4-phenoxyphenyl)-N'-carbomethoxy-S-methylisothiourea, m.p. 138° C.

EXAMPLE 4

By employing 2-amino-5-phenoxybutyranilide, m.p. 118° C, and N-(methylmercaptochloromethylene)-carbamic acid ethyl ester in the procedure of Example 1, part C, there is obtained N-(2-butyramido-4-phenoxyphenyl)-N'-carbethoxy-S-methylisothiourea.

EXAMPLE 5

In a manner analogous to that described in Examples 1C, 3 and 4, N-(methylmercaptochloromethylene)-carbamic acid methyl ester is allowed to react individually with a. 2-cyclohexanecarboxamido-4-phenoxyaniline, m.p. 142° C.,
b. 2-benzamido-4-phenoxyaniline, m.p. 140° C.,
c. 2-acetamido-4-(4-chlorophenoxy)aniline, m.p. 150°–151° C.,
d. 2-propionamido-4-(3-methoxyphenoxy)aniline, m.p. 129°–130° C.,
e. 2-methoxyacetamido-4-phenoxyaniline, m.p. 90° C.,
f. 2-propionamido-5-phenoxyaniline, m.p. 110°–111° C.,
g. 2-butyramido-4-phenylthioaniline, m.p. 152° C.,
h. 2-propionamido-4-phenylthioaniline, m.p. 145° C.,
i. 2-methoxyacetamido-4-phenylthioaniline, m.p. 145° C.,
j. 2-propionamido-4-(3-methoxyphenylthio)aniline, m.p. 107°–108° C.,
k. 2-acetamido-4-(4-chlorophenylthio)aniline, m.p. 150°–151° C.,
l. 2-butyramido-4-phenylsulfinylaniline, m.p. 152° C.,
m. 2-propionamido-4-phenylsulfinylaniline, m.p. 145° C.,
n. 2-propionamino-4-(3-methoxyphenylsulfinyl)aniline, m.p. 107°–108° C., and
o. 2-acetamido-4-(4-chlorophenylsulfinyl)aniline, m.p. 150°–151° C.

There are thus respectively obtained:

a. N-(2-cyclohexanecarboxamido-4-phenoxyphenyl)-N'-carbomethoxy-S-methylisothiourea, m.p. 168° C.,
b. N-(2-benzamido-4-phenoxyphenyl)-N'-carbamethoxy-S-methylisothiourea, m.p. 144° C.,
c. N-[2-acetamido-4-(4-chlorophenoxy)phenyl]-N'-carbomethoxy-S-methylisothiourea, m.p. 193° C.,
d. N-[2-propionamido-4-(3-methoxyphenoxy)phenyl]-N'-carbomethoxy-S-methylisothiourea, m.p. 136°–137° C.,
e. N-(2-methoxyacetamido-4-phenoxyphenyl)-N'-carbomethoxy-S-methylisothiourea, m.p. 145° C.,
f. N-(2-propionamido-5-phenoxyphenyl)-N'-carbomethoxy-S-methylisothiourea, m.p. 136°–137° C.,
g. N-(2-butyramido-4-phenylthiophenyl)-N'-carbomethoxy-S-methylisothiourea, m.p. 116° C.,
h. N-(2-propionamido-4-phenylthiophenyl)-N'-carbomethoxy-S-methylisothiourea, m.p. 112° C.,
i. N-(2-methoxyacetamido-4-phenylthiophenyl)-N'-carbomethoxy-S-methylisothiourea, m.p. 146° C.,
j. N-[2-propionamido-4-(3-methoxyphenylthio)phenyl]-N'-carbomethoxy-S-methylisothiourea, m.p. 136°–137° C.,
k. N-[2-acetamido-4-(4-chlorophenylthio)phenyl]-N'-carbomethoxy-S-methylisothiourea, m.p. 193° C.,
l. N-(2-butyramido-4-phenylsulfinylphenyl)-N'-carbomethoxy-S-methylisothiourea, m.p. 116° C.,
m. N-(2-propionamido-4-phenylsulfinylphenyl)-N'-carbomethoxy-S-methylisothiourea, m.p. 112° C., n. N-[2-propionamido-4-(3-methoxyphenylsulfinyl)-phenyl]-N'-carbomethoxy-S-methylisothiourea, m.p. 136°–137° C., and
o. N-[2-acetamido-4-(4-chlorophenylsulfinyl)-phenyl]-N'-carbomethoxy-S-methylisothiourea, m.p. 193° C.

EXAMPLE 6

The 2-amido-4-substituted anilines shown in the following table are employed in the manner described in Example 1, part C.

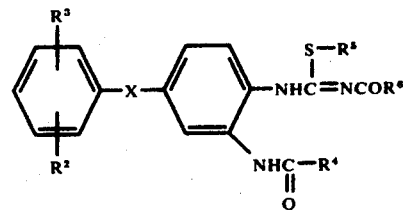

| | $R^3$ | X | $R^4$ |
|---|---|---|---|
| (a) | H | O | —$OCH_3$ |
| (b) | H | O | —$OC_2H_5$ |
| (c) | H | S | —$CH_2OC_6H_5$ |
| (d) | H | S | —$CH_2OC_2H_5$ |
| (e) | H | S | —$C_6H_5$ |
| (f) | H | S | —n-$C_4H_9$ |
| (g) | H | S | —n-$C_5H_{11}$ |
| (h) | H | S | —$NHCH_3$ |
| (i) | H | SO | —$CH_3$ |
| (j) | H | SO | —$OC_2H_5$ |
| (k) | H | SO | —cyclohexyl |
| (l) | H | SO | —$CH_2OCH_3$ |
| (m) | H | SO | —$CH_2OC_6H_5$ |
| (n) | H | SO | —$CH_2OC_2H_5$ |
| (o) | H | SO | —$C_6H_5$ |
| (p) | H | SO | —n-$C_4H_9$ |
| (q) | H | SO | —n-$C_5H_{11}$ |
| (r) | 4-$CH_3$ | SO | —$C_3H_7$ |

There are thus respectively obtained the following compounds:

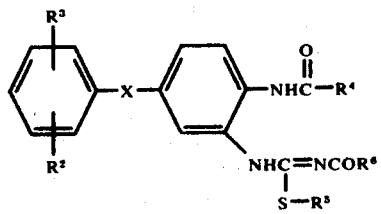

| | $R^3$ | X | $R^4$ |
|---|---|---|---|
| (a) | H | O | —$OCH_3$ |
| (b) | H | O | —$OC_2H_5$ |
| (c) | H | S | —$CH_2OC_6H_5$ |
| (d) | H | S | —$CH_2OC_2H_5$ |
| (e) | H | S | —$C_6H_5$ |
| (f) | H | S | —n-$C_4H_9$ |
| (g) | H | S | —n-$C_5H_{11}$ |
| (h) | H | S | —$NHCH_3$ |
| (i) | H | SO | —$CH_3$ |
| (j) | H | SO | —$OC_2H_5$ |
| (k) | H | SO | —cyclohexyl |
| (l) | H | SO | —$CH_2OCH_3$ |
| (m) | H | SO | —$CH_2OC_6H_5$ |
| (n) | H | SO | —$CH_2OC_2H_5$ |
| (o) | H | SO | —$C_6H_5$ |
| (p) | H | SO | —n-$C_4H_9$ |
| (q) | H | SO | —n-$C_5H_{11}$ |
| (r) | 4-$CH_3$ | SO | —$C_3H_7$ |

What is claimed is:

1. A compound selected from the group consisting of a 4-substituted-2-amidophenylisothiourea of the formula:

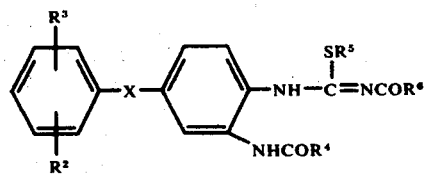

and a 5-substituted-2-amidophenylisothiourea of the formula:

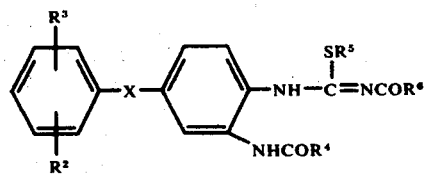

wherein X is sulfur, sulfinyl or sulfonyl;
$R^4$ is alkyl of 1 to 6 carbon atoms, cycloalkyl of 3 to 10 carbon atoms, phenyl, phenylalkyl of 7 to 12 carbon atoms, alkoxyalkyl of 2 to 12 carbon atoms, phenoxyalkyl of 7 to 12 carbon atoms;
$R^5$ is alkyl of 1 to 6 carbon atoms, alkenyl of 2 to 6 carbon atoms or alkynyl of 2 to 6 carbon atoms; and
$R^6$ is alkoxy of 1 to 6 carbon atoms, alkenyloxy of 2 to 6 carbon atoms, alkynyloxy of 2 to 6 carbon atoms, or alkoxyalkoxy of 2 to 12 carbon atoms:
each of $R^2$ and $R^3$ independent of the other is hydrogen, halogeno, alkyl of 1 to 6 carbon atoms, alkoxy of 1 to 6 carbon atoms, alkylthio of 1 to 6 carbon atoms, trifluoromethyl, alkanoyl of 1 to 6 carbon atoms, amino, alkanoylamino of 1 to 6 carbon atoms, or carbalkoxy of 2 to 7 carbon atoms.

2. A compound according to claim 1 in which said compound is of the formula:

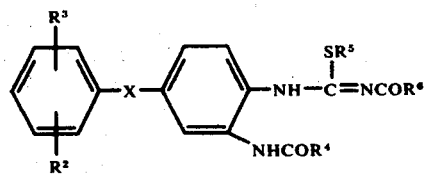

wherein
$R^4$ is alkyl of 1 to 6 carbon atoms, cycloalkyl of 3 to 7 carbon atoms, alkoxyalkyl of 2 to 8 carbon atoms, phenyl, benzyl, phenethyl or phenoxymethyl;
$R^5$ is alkyl of 1 to 4 carbon atoms, alkenyl of 2 to 4 carbon atoms, or alkynyl of 2 to 4 carbon atoms;
$R^6$ is alkoxy of 1 to 4 carbon atoms, alkenyloxy of 2 to 4 carbon atoms, alkynyloxy of 2 to 4 carbon atoms, or alkoxyalkoxy of 2 to 8 carbon atoms; and
each of $R^2$ and $R^3$ independent of the other is hydrogen, fluoro, chloro, bromo, alkyl of 1 to 4 carbon atoms, alkoxy of 1 to 4 carbon atoms, alkylthio of 1 to 4 carbon atoms, trifluoromethyl, alkanoyl of 2 to 4 carbon atoms, amino, alkanoylamino of 2 to 4 carbon atoms or carbalkoxy of 2 to 7 carbon atoms.

3. A compound according to claim 2 wherein X is sulfur.

4. A compound according to claim 3 wherein
R$^4$ is alkyl of 1 to 6 carbon atoms, alkoxyalkyl of 2 to 8 carbon atoms, cycloalkyl of 3 to 7 carbon atoms, phenyl, or phenoxymethyl;
R$^5$ is alkyl of 1 to 4 carbon atoms; and
R$^6$ is alkoxy of 1 to 4 carbon atoms.

5. A compound according to claim 2 wherein X is sulfinyl.

6. A compound according to claim 5 wherein
R$^4$ is alkyl of 1 to 6 carbon atoms, alkoxyalkyl of 2 to 8 carbon atoms, cycloalkyl of 3 to 7 carbon atoms, phenyl, or phenoxymethyl;
R$^5$ is alkyl of 1 to 4 carbon atoms; and
R$^6$ is alkoxy of 1 to 4 carbon atoms.

7. A compound according to claim 2 wherein X is sulfonyl.

8. A compound according to claim 7 wherein
R$^4$ is alkyl of 1 to 6 carbon atoms, alkoxyalkyl of 2 to 8 carbon atoms, cycloalkyl of 3 to 7 carbon atoms, phenyl, or phenoxymethyl;
R$^5$ is alkyl of 1 to 4 carbon atoms; and
R$^6$ is alkoxy of 1 to 4 carbon atoms.

9. A compound according to claim 1 in which said compound is of the formula:

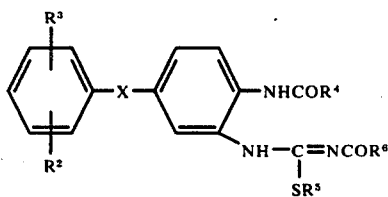

wherein
R$^4$ is alkyl of 1 to 6 carbon atoms, cycloalkyl of 3 to 7 carbon atoms, alkoxyalkyl of 2 to 8 carbon atoms, phenyl, benzyl, phenethyl or phenoxymethyl;
R$^5$ is alkyl of 1 to 4 carbon atoms, alkenyl of 2 to 4 carbon atoms, or alkynyl of 2 to 4 carbon atoms;
R$^6$ is alkoxy of 1 to 4 carbon atoms, alkenyloxy of 2 to 4 carbon atoms, alkynyloxy of 2 to 4 carbon atoms, or alkoxyalkoxy of 2 to 8 carbon atoms; and
each of R$^2$ and R$^3$ independent of the other is hydrogen, fluoro, chloro, bromo, alkyl of 1 to 4 carbon atoms, alkoxy of 1 to 4 carbon atoms, alkylthio of 1 to 4 carbon atoms, trifluoromethyl, alkanoyl of 2 to 4 carbon atoms, amino, alkanoylamino of 2 to 4 carbon atoms or carbalkoxy of 2 to 7 carbon atoms.

10. A compound according to claim 9 wherein X is sulfur.

11. A compound according to claim 10 wherein
R$^4$ is alkyl of 1 to 6 carbon atoms, alkoxyalkyl of 2 to 8 carbon atoms, cycloalkyl of 3 to 7 carbon atoms, phenyl, or phenoxymethyl;
R$^5$ is alkyl of 1 to 4 carbon atoms; and
R$^6$ is alkoxy of 1 to 4 carbon atoms.

12. A compound according to claim 9 wherein X is sulfinyl.

13. A compound according to claim 12 wherein
R$^4$ is alkyl of 1 to 6 carbon atoms, alkoxyalkyl of 2 to 8 carbon atoms, cyaloalkyl of 3 to 7 carbon atoms, phenyl, or phenoxymethyl;
R$^5$ is alkyl of 1 to 4 carbon atoms; and
R$^6$ is alkoxy of 1 to 4 carbon atoms.

14. A compound according to claim 9 wherein X is sulfonyl.

15. A compound according to claim 14 wherein
R$^4$ is alkyl of 1 to 6 carbon atoms, alkoxyalkyl of 2 to 8 carbon atoms, cycloalkyl of 3 to 7 carbon atoms, phenyl, or phenoxymethyl;
R$^5$ is alkyl of 1 to 4 carbon atoms; and
R$^6$ is alkoxy of 1 to 4 carbon atoms.

16. The compound according to claim 1 which is N-(2-butyramido-4-phenylthiophenyl)-N'-carbomethoxy-S-methylisothiourea.

17. The compound according to claim 1 which is N-(2-propionamido-4-phenylthiophenyl)-N'-carbomethoxy-S-methylisothiourea.

18. The compound according to claim 1 which is N-(2-methoxyacetamido-4-phenylthiophenyl)-N'-carbomethoxy-S-methylisothiourea.

19. A pharmaceutical composition comprising an anthelmintically effective amount of a compound according to claim 1 and a pharmaceutically acceptable diluent or carrier.

20. The method of combatting helmintic infestation in humans and animals which comprises administering to a human or animal an anthelmintically effective amount of a compound according to claim 1.

* * * * *